United States Patent
Overes et al.

(10) Patent No.: US 10,092,302 B2
(45) Date of Patent: Oct. 9, 2018

(54) COUPLING DEVICE FOR MEDICAL INSTRUMENT OR MEDICAL POWER-TOOL CHUCK

(71) Applicant: 4lmedical AG, Bettlach (CH)

(72) Inventors: Tom Overes, Langendorf (CH); Robert Frigg, Bettlach (CH)

(73) Assignee: 41 medical AG, Bettlach (CH)

( * ) Notice: Subject to any disclaimer, the term of this patent is extended or adjusted under 35 U.S.C. 154(b) by 275 days.

(21) Appl. No.: 14/906,202

(22) PCT Filed: Jul. 14, 2014

(86) PCT No.: PCT/CH2014/000103
§ 371 (c)(1),
(2) Date: Jan. 19, 2016

(87) PCT Pub. No.: WO2015/006876
PCT Pub. Date: Jan. 22, 2015

(65) Prior Publication Data
US 2016/0157871 A1    Jun. 9, 2016

(30) Foreign Application Priority Data

Jul. 19, 2013 (CH) ................................ 1287/13

(51) Int. Cl.
| A61B 17/16 | (2006.01) |
| B25B 23/00 | (2006.01) |
| A61B 17/88 | (2006.01) |
| B25G 3/04 | (2006.01) |
| B25G 3/18 | (2006.01) |
| A61B 17/00 | (2006.01) |

(52) U.S. Cl.
CPC ............ A61B 17/162 (2013.01); A61B 17/16 (2013.01); A61B 17/88 (2013.01);
(Continued)

(58) Field of Classification Search
CPC .......... A61B 2017/00477; A61B 17/16; A61B 17/162; B25G 3/04; B25G 3/02;
(Continued)

(56) References Cited

U.S. PATENT DOCUMENTS

| 4,938,107 A * | 7/1990 | Nickipuck .......... B25B 23/0035 |
| | | 403/365 |
| 6,733,218 B2 * | 5/2004 | Del Rio ............... A61B 17/162 |
| | | 279/79 |

(Continued)

FOREIGN PATENT DOCUMENTS

| CN | 201759601 U | 3/2011 |
| GB | 144607 A | 10/1920 |
| WO | WO 2009/129031 A1 | 10/2009 |

Primary Examiner — Jonathan P Masinick
(74) Attorney, Agent, or Firm — MU P.C.

(57) ABSTRACT

The present application relates to a coupling device for a handle (3) of a medical tool (1) or medical power-tool chuck (30). The coupling device comprises a coupling-body (2) including a bore (6), a working axis (X) extending along said bore (6) and a seat (4) arranged at a first end (8) of said bore for receiving a tool-insert (10) with a central axis (Y) at an angle in reference to the working axis (X). The coupling-body (2) further comprises a protrusion (7) arranged within said bore (6), said protrusion (7) being configured to engage a groove (13) of the tool-insert (10) upon alignment of the central axis (Y) with the working axis (X). The engagement of the protrusion (7) with said groove (13) locks the tool-insert (10) within said coupling body (2).

12 Claims, 12 Drawing Sheets

(52) U.S. Cl.
CPC ............ *B25B 23/0035* (2013.01); *B25G 3/04* (2013.01); *B25G 3/18* (2013.01); *A61B 17/8875* (2013.01); *A61B 2017/0046* (2013.01); *A61B 2017/00477* (2013.01)

(58) Field of Classification Search
CPC ........ B25G 3/18; B25G 3/26; B25B 23/0007; B25B 23/0035; B25B 23/0042
See application file for complete search history.

(56) References Cited

U.S. PATENT DOCUMENTS

| | | | |
|---|---|---|---|
| 7,653,970 B1* | 2/2010 | Lai ........................... | B25G 3/12 |
| | | | 16/422 |
| 7,942,826 B1* | 5/2011 | Scholl .................. | A61B 5/0492 |
| | | | 600/554 |
| 8,465,492 B2* | 6/2013 | Estes .................. | A61B 17/1615 |
| | | | 606/82 |
| 9,346,155 B2* | 5/2016 | Ivinson ............... | B25B 23/0035 |
| 2004/0220602 A1 | 11/2004 | Deng et al. | |
| 2005/0038443 A1* | 2/2005 | Hedley ................ | A61B 17/162 |
| | | | 606/91 |
| 2005/0235785 A1* | 10/2005 | Chang .................. | B25B 13/481 |
| | | | 81/177.75 |
| 2007/0017072 A1* | 1/2007 | Serio ....................... | A47L 13/42 |
| | | | 24/573.11 |
| 2014/0276839 A1* | 9/2014 | Forman .............. | A61B 17/1624 |
| | | | 606/80 |
| 2018/0126521 A1* | 5/2018 | Chou ................... | B25B 13/461 |

* cited by examiner

COUPLING DEVICE FOR MEDICAL INSTRUMENT OR MEDICAL POWER-TOOL CHUCK

TECHNICAL FIELD

The invention relates to a coupling device for a handle of a medical instrument or medical power-tool chuck as well as to a method for assembling a tool-insert into a coupling device of a medical instrument.

BACKGROUND ART

In many fields of surgery, for example orthopaedics, traumatology, spine surgery and dental surgery different tools, such as screwdriver shafts, drills, awls, probes, chisels, rasps are combined with handles.

In order to reduce costs, weight of instrument sets and number of instruments, tools are often designed as modular systems, featuring a small number of handles in different sizes and types which may be combined with a large number of different tool-inserts. For quick assembly and disassembly of different tool inserts during surgery, state of the art handles feature quick-couplings.

For example, GB 144,607 (Kunz Otto) discloses a tool with interchangeable blades. An offset portion of a blade provided on one side remote from the operative end bears on a handle and forms a pivot about which it is tilted by a movement of a clamping device. The blade is tilted until its back engages a groove provided at one end of the clamping device.

CN 201759601 U (Ningbo Jiandong Quinqzhou Machinery Technology Co.) describes a medical instrument which may be coupled with different tool-inserts. A handle comprises a slot for engaging a tool-insert, said slot comprising a slidable locking plate which locks the tool insert within the slot.

Existing couplings comprise complex and expensive mechanisms which have to fulfil different functional requirements. The coupling between handle and tool-insert must be able to resist high torsional moments, pull-out forces, compressive forces and impacts exerted to the tool by a surgeon. Furthermore, the coupling must be capable of being cleaned and sterilized prior to further surgeries such as to prevent cross-contamination between patients.

State of the art couplings comprise multiple moving parts in an assembly which may not be disassembled. Blood and other tissue may get caught in theses mechanisms and it is impossible to guarantee that all residues are removed before the instrument is used in a next surgery.

SUMMARY OF THE INVENTION

It is the object of the invention to create a coupling for a medical instrument which allows a quick and easy exchange of tool-inserts and which may be very easily and thoroughly cleaned and sterilized.

The solution of the invention is specified by the features of claim 1. According to the invention a coupling device for a handle of a medical tool or medical power-tool chuck comprises a coupling-body including a bore. A working axis extends along said bore whereby a seat is arranged at a first end of said bore for receiving a tool-insert with a central axis at an angle in reference to the working axis. The coupling-body further comprises a protrusion arranged within said bore, said protrusion being configured to engage a groove of the tool-insert upon alignment of the tool-insert central axis with the working axis, wherein engagement of said protrusion with said groove locks the tool-insert within said coupling body.

In this case the bore is more preferably aligned with a central axis of said handle or chuck. Preferably, the bore has a round cross-section. More preferably, the diameter of the bore is larger than the dimension of the cross-section of the tool-insert.

The seat is preferably configured as opening with a defined shape, e.g. round, rectangular or polygonal. More preferably, the seat includes an aperture in the shape of the tool-insert with dimensions corresponding to the cross section of the tool-insert.

The tool-insert may for example be a shaft of a screwdriver, drill, awl, chisel, rasp or probe.

The bore further includes a protrusion, which is preferably located towards said first end, i.e. in the vicinity of the seat. The protrusion may e.g. be in the form of a hemispherical nose. Preferably, the protrusion is in the form of a cylindrical pin. The central axis of said pin is preferably oriented at a right angle to said working axis, while the pin itself is located eccentrically in said bore, i.e. said pin causes a local constriction in the diameter of the bore.

The tool-insert is received at an angle in said bore, i.e. the central axis of the tool-insert is inclined in respect to the working axis of the bore. By inserting the tool-insert at an angle a first end of said tool-insert is guided past said protrusion. Upon alignment of said central axis with said working axis, the groove provided on said tool-insert engages said protrusion, thereby locking said tool-insert with said coupling-body.

Preferably, the groove has a cross section which has the same shape and dimension as the cross-section of said protrusion.

Thus the coupling device according to the present invention allows a very simple, yet effective coupling of a tool-insert in a handle of a medical tool or in a medical power-tool chuck. Specifically, while allowing a quick insertion and removal of a tool-insert, the coupling device provides for a transmission of torsional moments, Preferably, said coupling device includes a locking-body being mounted within the bore and being translatable about the working axis, wherein the locking-body is translatable from a first position in a second position, the locking-body locking the central axis of the tool-insert to the working axis in the second position.

This allows safely locking the tool-insert in the coupling device and prevents any unwanted uncoupling of the tool-insert from the coupling device.

Preferably, said locking-body is configured to be operated by a user of the medical tool or medical power-tool chuck, e.g. by means of a sliding button, rotary knob or the like. Further preferably, said locking-body comprises a catching mechanism such as to lock the locking-body in said second position such as to prevent any unwanted movement of said locking-body to said first position.

Preferably, said seat comprises at least one anti-rotation face mating with at least one corresponding face on the tool-insert such as to transfer a torque force between the coupling body and the tool-insert.

Said anti-rotation face is preferably configured as plane cooperating with a mating planar surface arranged on said tool-insert. For example, said anti-rotation face may be in the form of a flat surface in an otherwise round seat.

Preferably, said seat has a polygonal shape, e.g. in the form of a hexagonal bushing. Such a configuration allows a good transmission of torque forces from the medical tool or medical power-tool chuck to the tool-insert.

Alternatively, the at least one anti-rotation face may be arranged within said at least one bore, whereby said at least one anti-rotation face cooperates with a mating surface arranged on said tool-insert.

Preferably, the at least one anti-rotation face is a rounded anti-rotation face comprising a curved surface in the direction of the central axis. Provision of at least one rounded anti-rotation face facilitates the inclination of the tool-insert relative to the coupling body. Preferably, the tool-insert comprises a plurality of rounded anti-rotation faces, e.g. arranged in the form of a hexagon around the circumference of the tool-insert.

Preferably, said locking-body comprises a cylindrical hollow body having an outer diameter substantially equivalent to the diameter of the bore and a top portion with an increased diameter, said locking-body being inserted into the bore at a second end arranged opposite to said first end.

By translating said cylindrical hollow body to said second position, a circumferential wall of said cylindrical hollow body is pushed between a tool-insert end and an inner wall of said bore, hence preventing any inclination of the tool-insert within said bore. Therefore, the central axis of the tool-insert is fixed relative to the working axis of the bore. This prohibits the uncoupling of said protrusion from said groove and hence an unlocking of the tool-insert and the coupling body.

The top portion with the increased diameter serves as grip for an operator to move the cylindrical hollow body from said first position into said second position and vice versa. Further, said increased diameter limits the distance which the cylindrical hollow body may travel within the bore and thus prevents an over insertion of said cylindrical hollow body.

Alternatively, the locking-body is mounted into the bore at said first end and is configured to be tilted in relation to the working axis in the first position.

With this alternative embodiment, the locking-body is located at the same end of the coupling body as the seat. This facilitates the handling of the medical tool or medical power-tool chuck, as all operations may be carried out by an operator from the same side.

Further, as the medical tool is grasped by an operator towards the second end and the medical power-tool chuck is coupled to a power tool at the second end, placement of the locking-body at the first end minimizes the risk of an accidental unlocking of the locking-body during operation of the medical tool or medical power-tool chuck.

Preferably, the coupling body comprises a female drive geometry at its first end and the locking body includes a male drive geometry adapted to be engaged with said female drive geometry in the second position.

This allows the transmission of rotational moments, i.e. of torque from the coupling body to the locking body, as the male drive geometry and the female drive geometry are engaged in a form-fitting manner. Further, the locking body may thereby also be blocked from any translational movement from the second position back into the first position, which may lead to a loss of coupling between the tool-insert and the coupling body.

Preferably, the locking body includes an opening for passage of the tool-insert, said opening comprising at least one second anti-rotational face. Hence, through an interaction of said second anti-rotational faces with the at least one tool-insert face, any rotational moments or torque force applied onto said locking body may be transmitted to the tool-insert.

Preferably, the locking body further comprises a cylindrical portion linking said male drive geometry with a locking body sphere having a rounded outer surface, said cylindrical portion and said locking body sphere being sized to be inserted into said bore.

Provision of the locking body sphere with a rounded outer surface allows tilting the locking body relative to the coupling body in said first position. The cylindrical portion more preferably has a smaller diameter than said locking-body sphere. Further, at least one slit may be arranged on said locking-body sphere and said cylindrical portion, enabling some elasticity for an easier insertion and removal of said locking-body sphere and said cylindrical portion into or out of said bore.

Alternatively, the locking body may be configured to be slipped over said coupling body at the first end, wherein said coupling body includes a conical portion at its first end. The conical portion allows tilting of the locking body relative to the coupling body in said first position. Further, the conical portion also facilitates the assembly of the locking body onto the coupling body.

Preferably, the handle or chuck and the coupling-body are in the form of a mono-block component. In this application, the term "mono-block" means an item or an assembly of items having a completely closed outer surface. Preferably, the term mono-block refers to an item having several features integrally formed into one single piece having a closed outer surface. i.e., the handle or chuck and the coupling body are provided as a monolithic component. In a preferred embodiment, the handle of the medical tool or the medical power tool chuck are part of an integral, single item. Preferably, the tool-insert is likewise configured as a mono-block.

This guarantees that no blood or other tissue can get caught in small gaps, hinges or other mechanisms of the medical tool or medical power tool chuck, hence allowing the medical tool or medical power-tool chuck to be cleaned and sterilised in a far more optimal manner.

Further preferably, the protrusion is unitary with the coupling body. Hence, the protrusion and the coupling body are also configured as mono-block structure, hence further enhancing the efficiency of cleaning and sterilization.

The present application further relates to a method for assembling a tool-insert into a coupling device of a handle of a medical device or of a medical power-tool chuck. The tool-insert is inserted into a bore of the coupling device at an angle relative to a working axis of the bore, wherein a central axis of said tool-insert is subsequently aligned with said working axis. The alignment allows an engagement of a groove of the tool-insert with a protrusion arranged within said bore.

The coupling used in said method most preferably is a coupling device according to the present invention.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
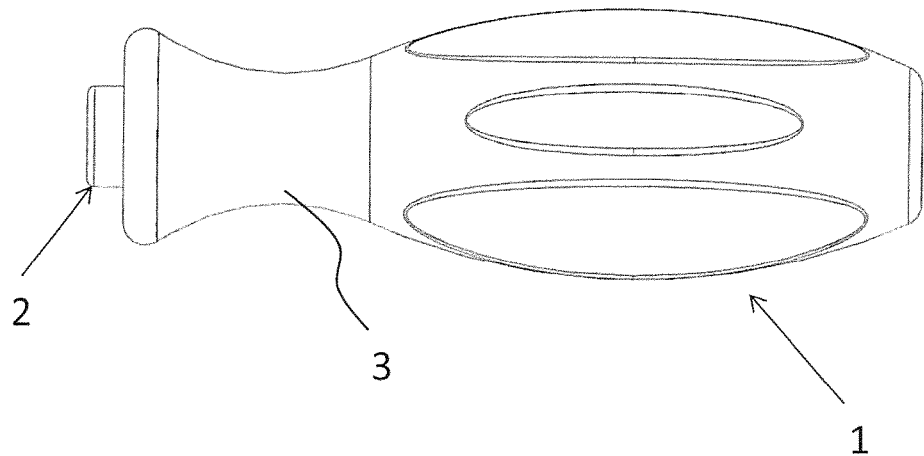
FIG. 1 A first embodiment of a medical tool with a coupling device according to the present invention.

FIG. 1 shows a medical tool 1 according to the present invention without a tool-insert. The medical tool 1 comprises a handle 3, which may be combined with different tool-inserts such as for example a screwdriver, a chisel or a rasp. The handle 3 comprises an outer portion designed for an ergonomic interaction with a hand of a surgeon. The material of the outer portion of the handle 3 may exemplarily be made of biocompatible silicon, which offers a comfortable soft touch and high friction to the hand of the surgeon. In the centre of the handle, a coupling body 2, preferably made of a metal, is incorporated. For example, the biocompatible silicone may be injection moulded over the coupling body 2.

Alternatively, the coupling body 2 and the handle 3 may be configured as a mono-block, i.e. a single part, for example out of a hard material such as steel, aluminium, titanium, a metal alloy or a high strength polymer.

Figure 2:
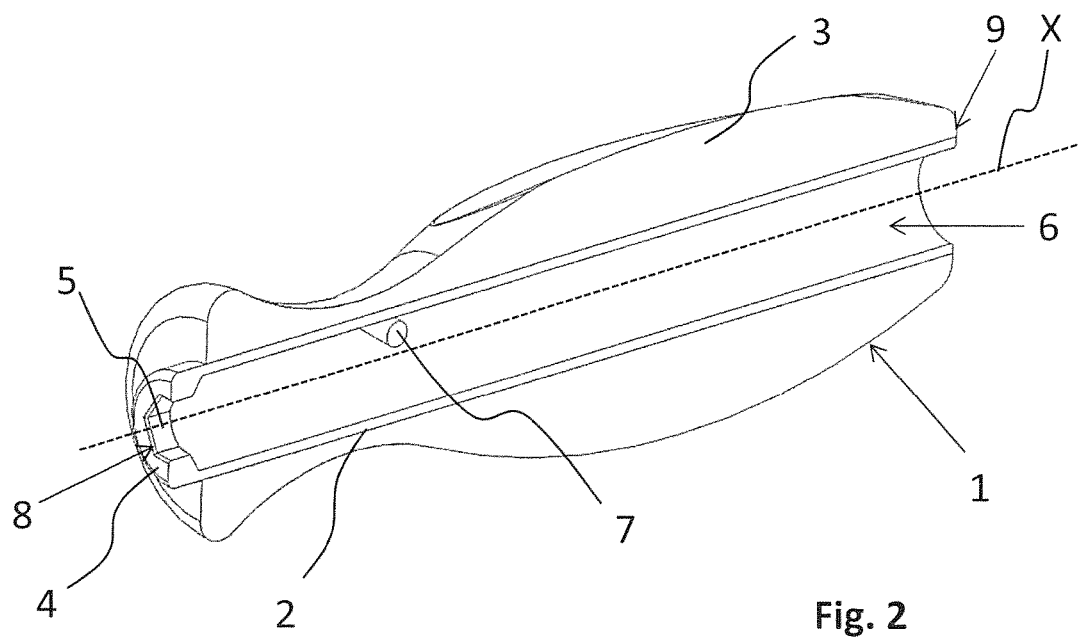
FIG. 2 a cross-sectional view of the medical tool according to FIG. 1.

FIG. 2 depicts a cross-sectional view of the medical tool 1 according to FIG. 1. The coupling body 2 arranged within handle 3 comprises critical geometries for the transfer of torsional moments, pull-out forces, compressive forces and impactions to and from a tool-insert during use of the medical tool 1. The coupling body 2 is configured as a hollow cylindrical body including a bore 6. In the embodiment shown, bore 6 is configured as through bore. A seat 4 is provided at a first end 8 of the coupling body 2. The seat 4 includes a flat front end intended to transfer any impaction forces from a tool-insert to the coupling body 2. Further, beneath the seat 4, the coupling body 2 includes anti-rotation faces 5. These anti-rotation faces 5 transmit any rotational moment to a tool-insert. In the embodiment shown, the coupling body 2 includes six anti-rotation faces 5 which are arranged in the form of a hexagon. However, any other number and/or arrangement of the anti-rotation faces 5 may be envisaged.

A working axis X spans trough the bore 6 from its first end 8 to a second end 9. The working axis X corresponds to a central length axis of the bore 6. A protrusion 7 is arranged within the bore 6. In the embodiment shown, the protrusion 7 is configured as pin arranged transversally to the working axis X and extending partially into the bore 6.

At the second end 9, the bore 6 is open such that further elements may be inserted through said second end 9 into said bore 6.

Figure 3:
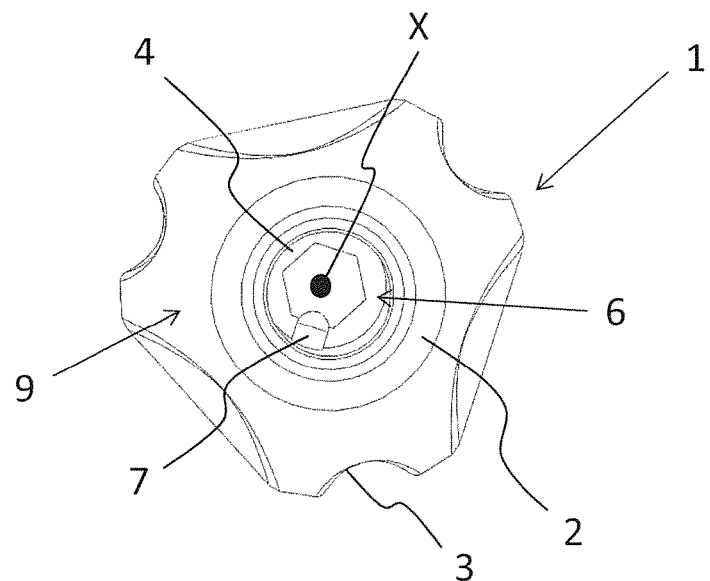
FIG. 3 a view of the medical tool according to FIG. 1 from the second end along the working axis.

FIG. 3 shows a view of the medical device as shown in FIGS. 1 and 2 from the second end 9 along the working axis X. As may be seen, the handle 3 has a shape designed for an ergonomic interaction with the hand of a surgeon. Furthermore, the extension of protrusion 7 into the inner space of bore 6 as well as its configuration as pin may be recognized in this figure. The arrangement of the anti-rotation faces 5 in the form of a hexagon is also apparent from this picture.

Figure 4:
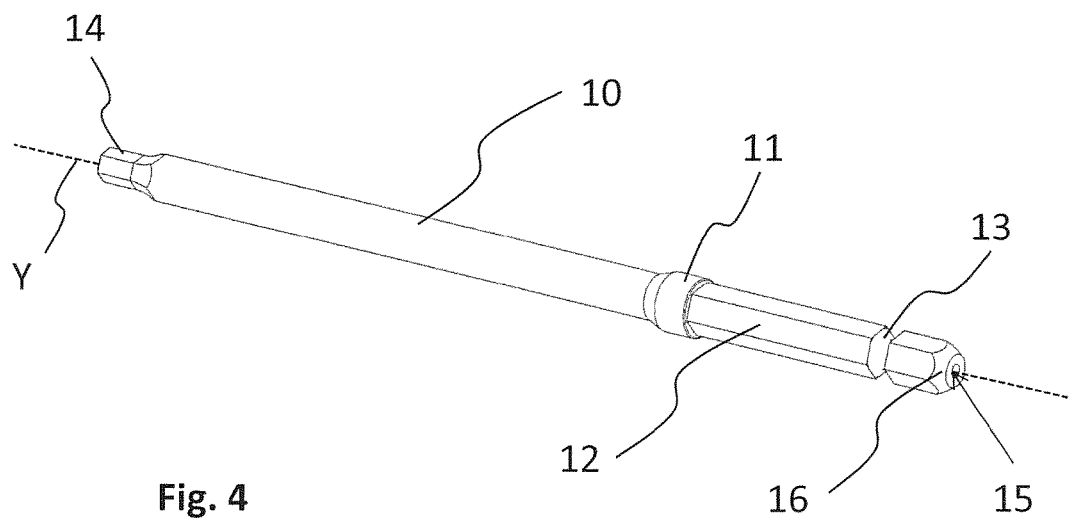
FIG. 4 a representation of a tool-insert according to the present invention.

FIG. 4 shows a representation of a tool-insert 10, which may be coupled to a handle 3 of a medical device 1 as shown in FIGS. 1 to 3. At one end, the tool-insert 10 comprises a tool-feature end 14, which is configured as a hexagonal drive in the embodiment shown. Alternatively, the tool-feature end 14 may be configured in the form of any other tool, such as a chisel, a rasp or the like. The tool-insert is generally configured in the shape of a cylinder, i.e. an elongate body with a round cross-section. However, depending on the intended use of the tool-insert 10, it may be configured as elongated body with a rectangular, oval or polygonal cross section. Further, the tool-insert 10 may be configured as elongate body with sections having different cross-sections, e.g. as shown in the present exemplary embodiment.

At its other end, the tool-insert 10 comprises a tool-insert end 15, which is intended to be inserted into the bore 6 of the coupling means 2 from the first end 8. The tool-insert end 15 includes a chamfer 16 which facilitates the insertion of the tool-insert 15 into the bore 6. Adjacent said tool-insert end 15, the tool-insert 10 comprises tool-insert faces 12. Once the tool-insert 10 is engaged into said bore 6 of the handle coupling body 2, the tool-insert faces 12 cooperate with the faces 5, whereby the tool-insert 10 and the coupling body 2 are engaged in a form-fitting connection. This allows the transmission of any torsional moments, i.e. of torque forces applied to the handle 3 to the tool-insert 10.

Towards the tool-feature end 14 of the tool-insert faces 12, an insert seat 11 having a bigger diameter than the tool-insert 10 is arranged. This insert seat 11 is intended to transmit impaction forces between the tool-insert 10 and the seat 4 of the coupling body 2. The groove 13 is sized and dimensioned such as to cooperate with the protrusion 7 in a form-fitting manner. The interaction between said groove 13 and the protrusion 7 allows the transfer of pull-out and compressive forces between the tool-insert 10 and the coupling body 2. Further details about the various interactions between the tool-insert 10 and the coupling body 2 may be derived from FIGS. 6a to 6c.

Figure 5:
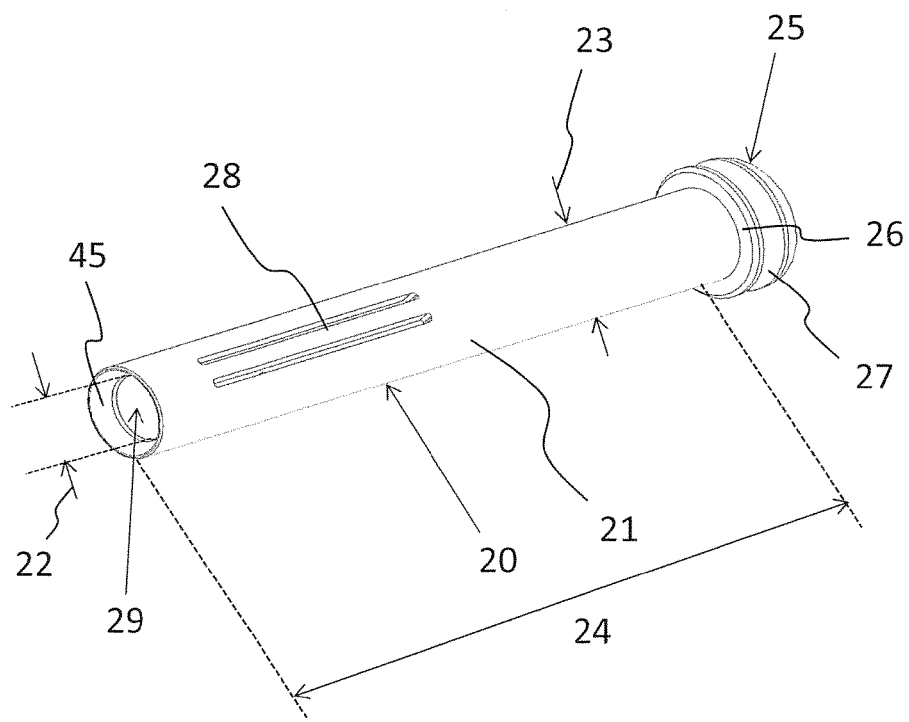
FIG. 5 a representation of a locking-body for the medical tool according to FIG. 1.

FIG. 5 is a representation of an exemplary locking-body 20 of the medical tool 1. The locking-body 20 comprises a cylindrical hollow body 21 with an open lumen 29. The cylindrical hollow body 21 comprises a top portion 25 with an increased diameter at one end. The diameter of the top portion 25 is larger than the diameter of the bore 6 of the coupling body 2, while an outer diameter 23 of the cylindrical hollow body 2 is smaller than the diameter of the bore 6. Hence, the cylindrical hollow body 21 may be inserted into bore 6 from the second end 9. The top portion 25 includes a stopper face 26 which limits the insertion of the cylindrical hollow body 21 into said bore 6. Further, a compliant structure 28 is arranged on the outer surface of the cylindrical hollow body 21. The compliant structure 28, which in the present embodiment comprises two parallel slits, allows the establishment of a friction fit between the locking-body 20 and the inner surface of the bore 6. Other mechanisms for locking the locking-body 20 with the inner surface of the bore 6 may be used, such as e.g. a threaded engagement.

Further, the top portion 25 comprises a notch 27 for handling purposes which facilitates the gripping of the top portion 25 by a surgeon. The length 24 of the cylindrical hollow body is smaller than the distance between the protrusion 7 and the second end 9 of the coupling body 2. Hence, any impaction forces exerted on the locking body 20 are transmitted to the coupling body 2 exclusively by means of the stopper face 26. It is understood that such impaction forces will subsequently be transmitted further to tool-insert 10 by means of the interaction between the seat 4 with the insert seat 11.

The inner diameter 22 of the cylindrical hollow body 21 is chosen such as to allow an insertion of the tool-insert 10 into the lumen 29. At the end which is on the opposite of the top portion 25, a chamfered region 45 is provided on the inner circumference of the cylindrical hollow body 21, hence providing a progressive enlargement of the inner diameter 22. This facilitates the advancement of the hollow cylindrical body onto a tool-insert 10.

Figure 6A:
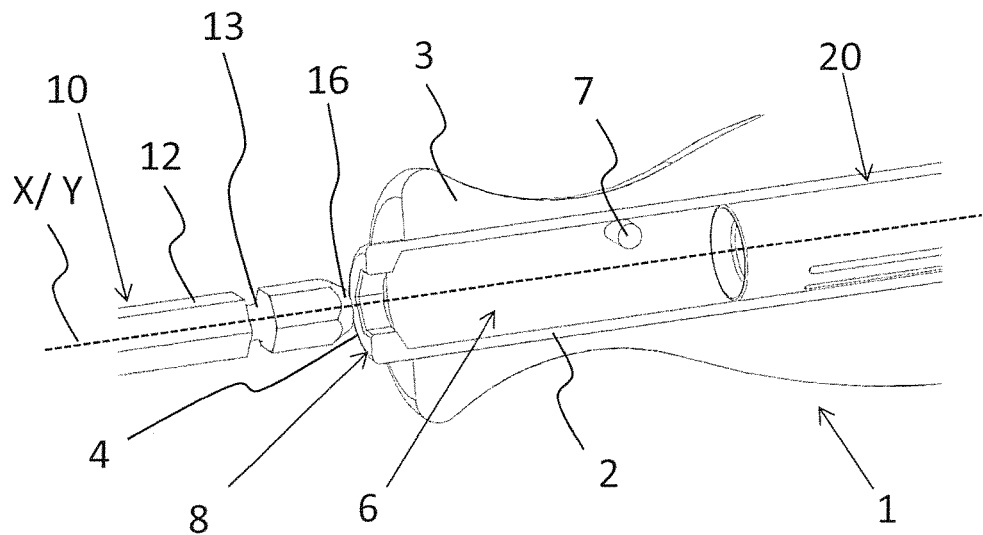
FIGS. 6a-6c the assembly steps of the medical tool according to FIG. 1 with the tool-insert according to FIG. 4.
Figure 6B:
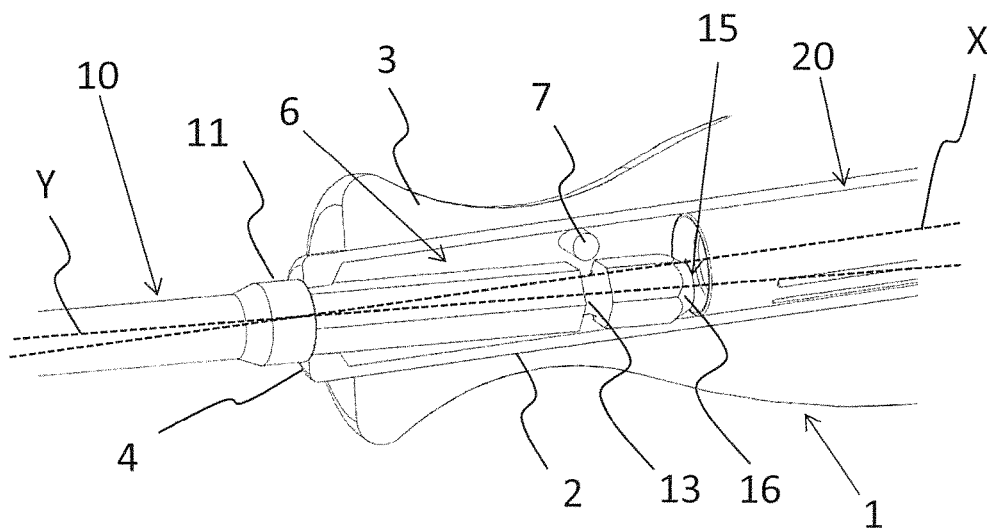
Figure 6C:
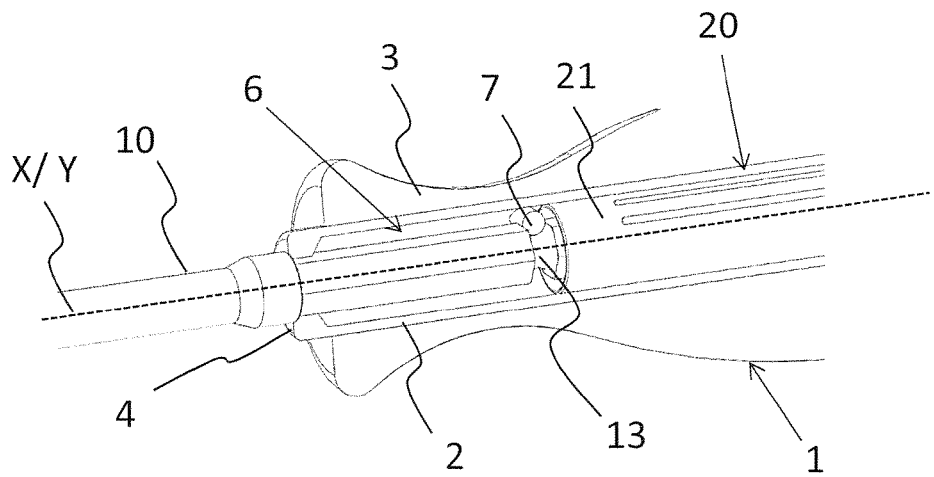

FIGS. 6*a*, 6*b* and 6*c* show the different assembly steps of a medical tool 1 in section drawings. FIG. 6*a* depicts a first step in the assembly process. The locking-body 20 is inserted into the bore 6 from the second end 9 (not shown in this figure) and partially advanced towards the first end 8. This corresponds to the first position of the locking body 20. Then, the tool-insert 10 is inserted into the bore 6 from the first end 8. The tool-insert 8 is thereby oriented in such a way that the tool-insert faces 12 match the faces 5 at the first end 8 of the coupling body 2 and that a central axis Y of the tool-insert is oriented to be congruent with the working axis X of the coupling insert 2. The chamfer 16 facilitates the insertion of the tool-insert 10 between the faces 15.

FIG. 6*b* depicts a second step of the assembly of medical tool 1. After the first step as shown in FIG. 6*a*, the tool-insert 10 is further advanced towards the second end 9. As soon as the tool-insert end 15 reaches the protrusion 7, the tool-insert 10 is inclined relative to the coupling body 2, such that the central axis Y is at an angle with the working axis X. In this way, the tool-insert 10 may be further advanced past the protrusion 7. The chamfer 16 facilitates the passage of the tool-insert end 15 past the protrusion 7, as it provides a guiding surface leading to the inclination of the tool-insert 10 relative to the coupling body 2. The maximum angulation of the tool-insert 10 relative to the coupling body 2 is dependent on the amount of play between insert-tool faces 15 and faces 4. Of course, the play should be sufficient to allow an inclination which allows the passage of the tool-insert end 15 along protrusion 7.

The length of the portion of the tool-insert 10 between the insert seat 11 and the groove 13 matches the distance between seat 4 and protrusion 7 of the coupling body 2. Hence, when the insert seat 11 comes into contact with seat 4, the groove 13 is aligned with the protrusion 7. In this position, the tool-insert 10 is moved back in a parallel position to the coupling body 2, such that the central axis Y and the working axis X are re-aligned. By doing so, protrusion 7 will hook into or be biased into engagement with groove 13.

FIG. 6*c* shows the final step in the assembly of medical tool 1. Once the protrusion 7 is engaged within groove 13, the locking-body 20 is advanced towards the first end 8.

Thereby, the hollow cylindrical body 21 is inserted between the tool-insert end 15 and the inner circumference of the tube 6, blocking any play between tool-insert 10 and the inner circumference of the bore 6, hence eliminating any movement or inclination of the tool-insert 10 relative to the locking body 20. This effectively locks the protrusion 7 in the groove 13. The state where the locking body 20 is fully inserted into the bore 6 corresponds to the second position of the locking body.

Figure 7A:
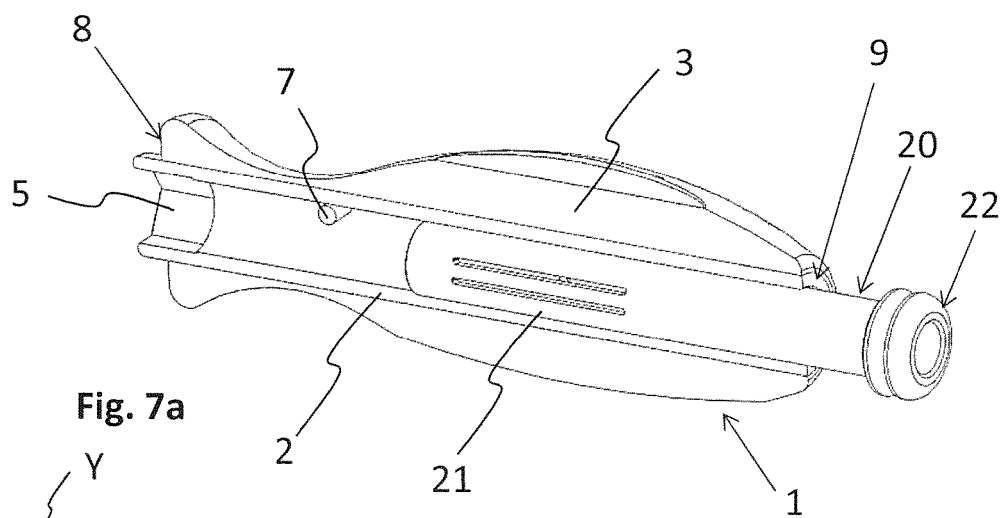
FIGS. 7a-7b a second embodiment of a medical tool with a coupling device according to the present invention and of an appropriate tool-insert.
Figure 7B:
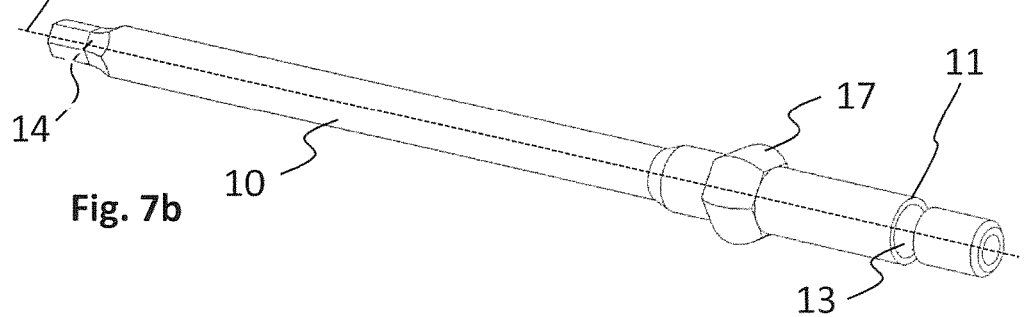

FIGS. 7*a* and 7*b* show a second embodiment of a medical tool 1 according to the present invention. FIG. 7*a* shows the handle 3 with the coupling body 2 integrated therein. At the first end, the coupling body 2 comprises anti-rotation faces 5, but no seat 4. Otherwise, the handle 3 and the coupling body 2 have the same features as the embodiment as shown in FIGS. 1 to 6.

Figure 8A:
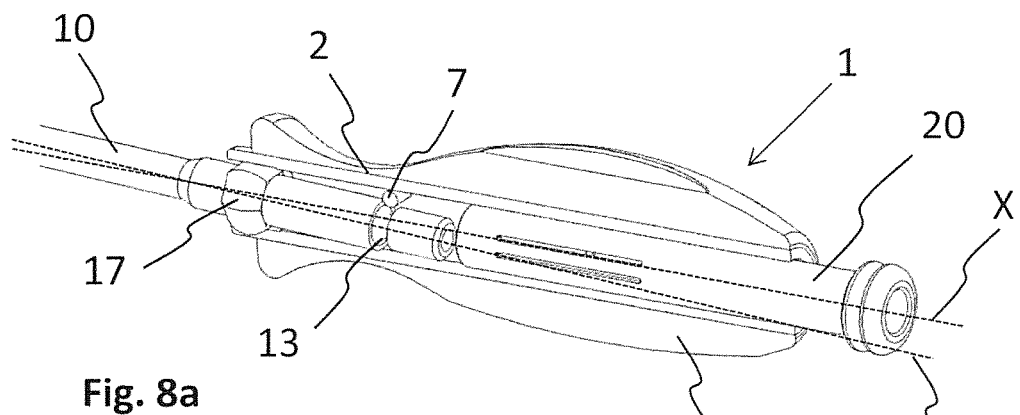
FIGS. 8a-8c the assembly steps of the second medical tool with the tool-insert.

The tool-insert 10 is depicted in FIG. 7*b*. In contrast to the embodiment as shown in FIGS. 1 to 6, the tool-insert 10 comprises rounded faces 17. Rounded faces 17 do not include a flat surface as the tool-insert faces 12, but rather exhibit a curved surface in the direction of the central axis Y. This curvature of the rounded faces 17 facilitates the inclination of the tool-insert 10 relative to the coupling body 2, as is shown in FIG. 8*a*. Hence, contrary to the embodiment as shown in FIGS. 1 to 6, where inclination of the tool-insert 10 relative to the coupling body 2 is relying on some play between the anti-rotation faces 5 and the tool-insert faces 12, in this embodiment the inclination is easily achieved by a kind of rolling motion between the rounded faces 17 and the anti-rotation faces 5. Further, the insert seat 11 is not arranged besides the rounded faces 17, but adjacent the groove 13 in this embodiment.

Figure 8B:
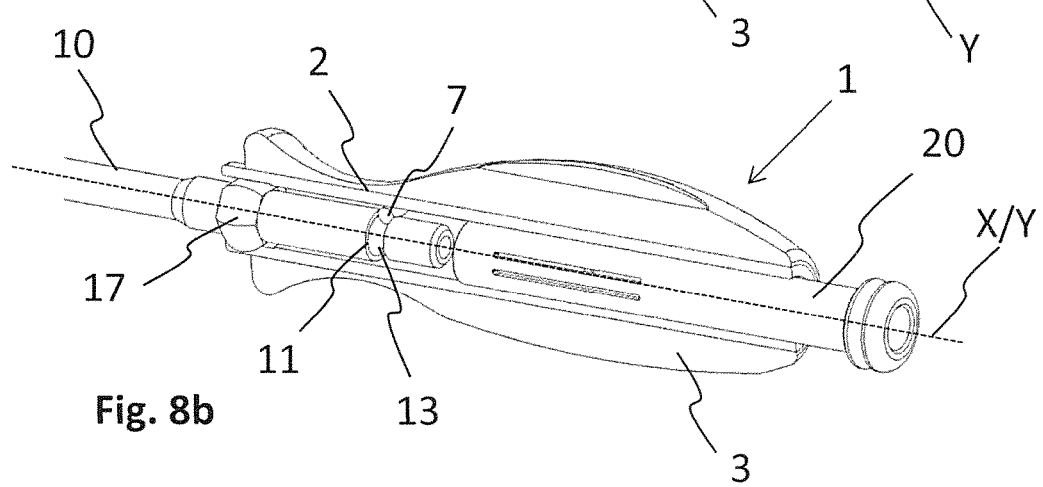
Figure 8C:
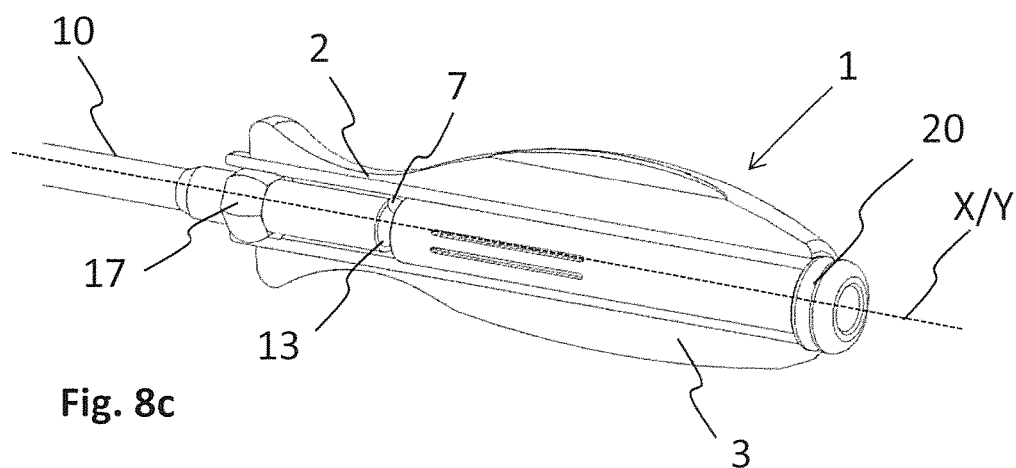

FIGS. 8*a* to 8*c* show the assembly steps for a medical tool 1 according to the embodiment as depicted in FIGS. 7*a* and 7*b*. FIG. 8*a* already shows the second step of the assembly, as the first step is identical to the first step as shown for the first embodiment of the medical tool 1 on FIG. 6*a*. As may be seen on this figure, the cooperation of the rounded faces 17 with the faces 4 facilitates the inclination of the tool-insert 10 relative to the coupling body 2.

As may be seen on FIG. 8*b*, upon re-alignment of the central axis Y with the working axis X, the protrusion 7 engages the groove 13. However, in difference to the first embodiment as shown in FIGS. 1 to 6, the insert seat 11 cooperates with the protrusion 7 rather than with a seat 4. Therefore, any impaction forces exerted on tool-insert 10 will be transmitted to the coupling body 2 via the interaction of the insert seat 11 and the protrusion 7.

Analogous to the first embodiment, the locking-body 20 is finally advanced towards the first end 8 and hence the second position, whereby the cylindrical hollow body will be inserted between the tool-insert end 15 and the inner circumference of the bore 6, thereby blocking any inclination of the tool-insert 10 relative to the coupling body 2.

Figure 9A:
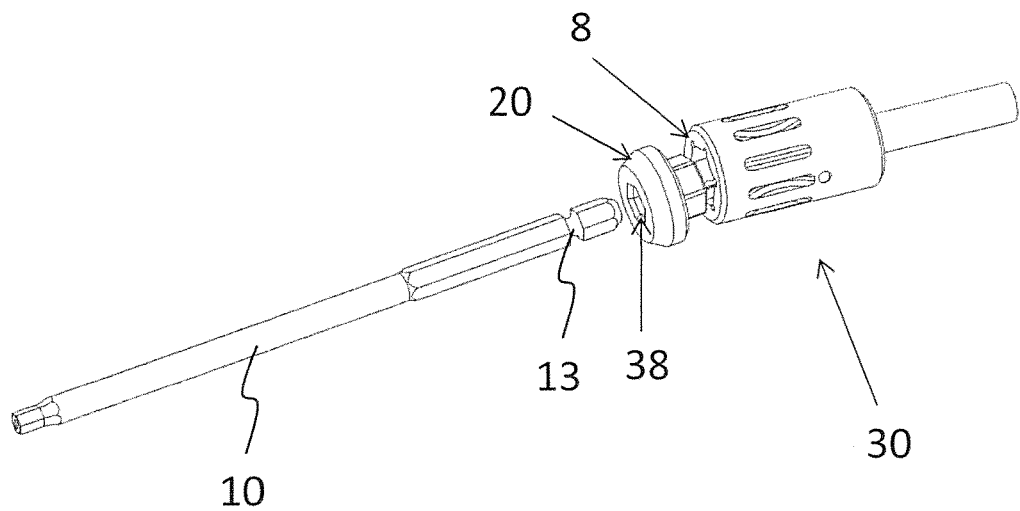
FIGS. 9a-9b an embodiment of a medical power-tool chuck with a coupling body according to the present invention and an appropriate tool-insert.
Figure 9B:
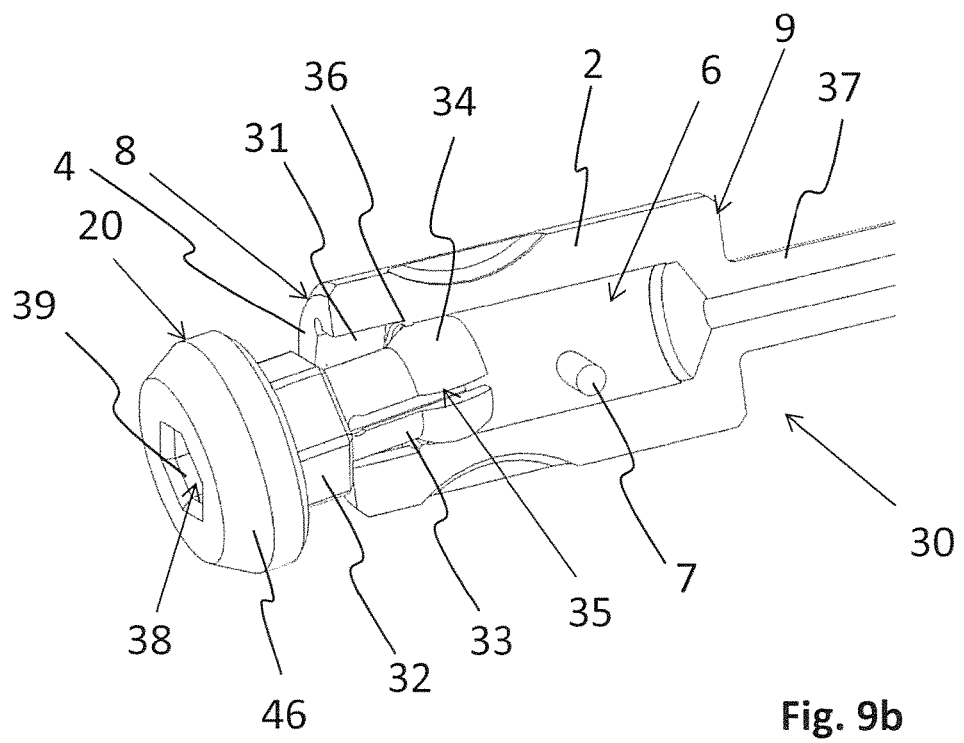

FIGS. 9*a* and 9*b* show an exemplary embodiment of a medical power tool chuck 30 according to the present invention. Contrary to the two embodiments of a medical tool 1 as shown in FIGS. 1 to 8, the locking body 20 is inserted into the bore 6 of the coupling body 2 from the first end 8. Further, the locking body comprises an opening 38 through which the tool insert 10 may be passed such as to be inserted into the bore 6. It is understood that the same tool inserts 10 as used in connection with the first embodiment of a medical tool 1 as shown in FIGS. 1 to 6 may be used in connection with the medical power chuck 30 according to the present embodiment.

FIG. 9b shows a detailed sectional view of the coupling body 2 and its interaction with the locking body 20. The coupling body 2 is affixed to a connection portion 37 at its second end 9. The connection portion may transmit movement or force, such as e.g. a torque from the power tool to the coupling body 2. The bore 6 is configured as blind hole having the protrusion 7 arranged therein. At the first end 8 the coupling body 2 includes a female drive geometry 31 having multiple flat surfaces, e.g. six surfaces arranged in the form of a hexagon. Additionally, a rim 36 is arranged between the female drive geometry 31 and the remainder of the bore 6.

The locking body 20 comprises a head section 46 including the opening 38, a male drive geometry 32, a cylindrical portion 33 as well as a locking-body sphere 34. The locking-body sphere 34 and the cylindrical portion 33 are configured to be inserted into the bore 6 from the first end 8, while the male drive geometry is shaped and dimensioned such as to form-fittingly cooperate with the female drive geometry 31 of the coupling body 2. The head section 46 has an enlarged diameter which preferably corresponds to the outer diameter of the coupling body 2. At least two cut-outs 35 (of which only one is visible in FIG. 9b) running along said cylindrical portion 33 and said locking-body sphere 35 in a direction which is parallel to a central axis of said cylindrical portion 33.

The locking-body sphere 34 has a rounded outer surface which allows inclining the locking body 20 relative to the coupling body 2. The cut out 15 imparts some elasticity to the cylindrical portion 33 and the locking body sphere 34, thus facilitating the assembly and disassembly of the locking body 20 into the coupling body 2. The diameter of the bore 6 is locally reduced by means of the rim 36, preventing an unintentional removal of locking body 20 from coupling body 2. However, due to the elasticity caused by the at least two cut-outs 35, the locking body 20 may nonetheless be removed, e.g. for cleaning and sterilization.

The form-fitting cooperation of the male drive geometry 32 with the female drive geometry 31 allows the transmission of torsional moments or torque from the coupling body 2 to the locking body 20 and vice versa. Further, the opening 38 comprises second anti-rotational faces 39 which may cooperate with tool-insert faces 12 for the transmission of torsional moments or torque from the locking body 20 to the tool-insert 10.

Figure 10A:
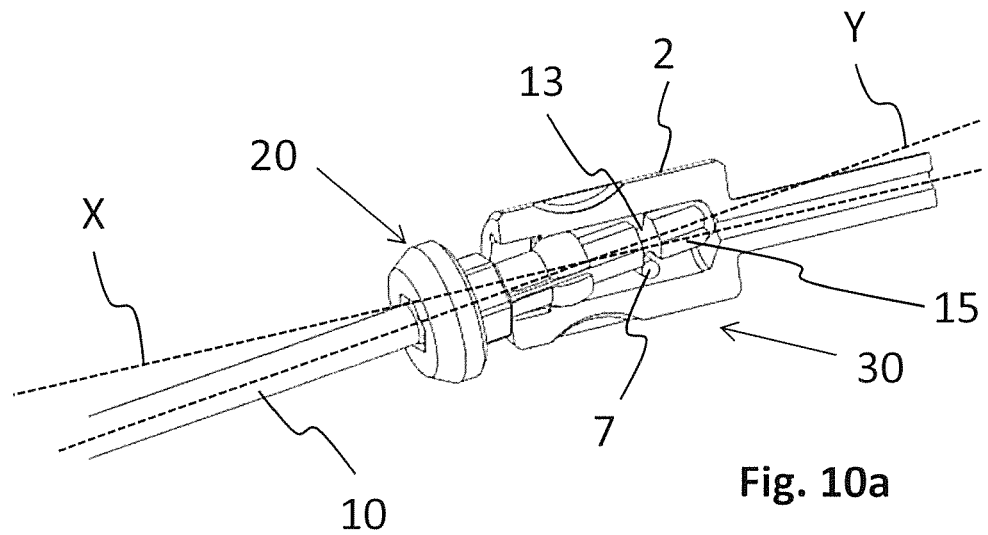
FIGS. 10a-10c the assembly steps of the medical power-tool chuck according to FIG. 9 with the tool-insert.
Figure 10B:
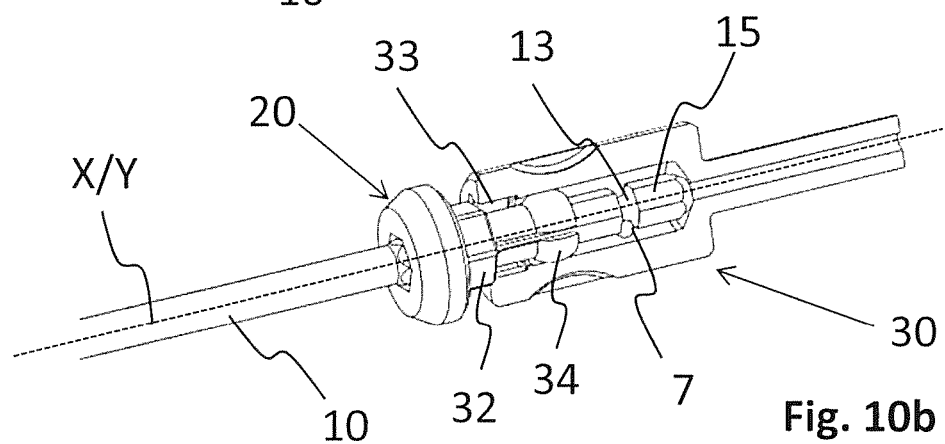
Figure 10C:
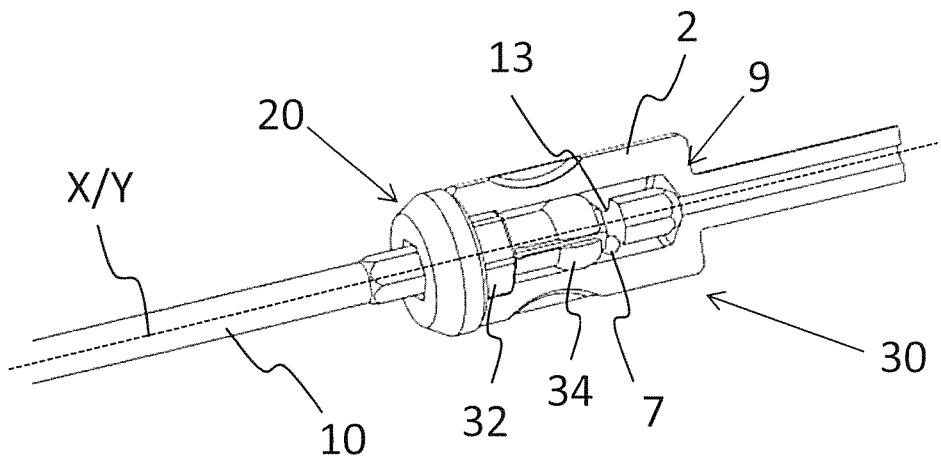

FIGS. 10a to 10c depict the assembly steps for the medical power tool chuck 30 according to the embodiment as shown in FIGS. 9a and 9b. In a first step, the tool-insert 10 is introduced into the opening 38, while the blocking body 20 is in an inclined position relative to the coupling body 2. This inclined position results in an inclination of the central axis Y of the tool-insert 10 relative to the working axis X of the coupling body 2 and corresponds to the first position of the locking body 20. In this way, the tool-insert end 15 may be passed alongside protrusion 7. As mentioned earlier, the tool-insert faces 12 enter into a form-fit engagement with the second anti-rotational faces 39 of opening 38.

When the tool-insert 10 is inserted sufficiently deep into the bore 6 for the groove 13 to engage the protrusion 7, the central axis Y is re-aligned with the working axis X by tilting the blocking body 20 in a position where it is parallel to the coupling body 2, as shown in FIG. 10b. Typically, the tool-insert 10 will be dimensioned such that this position is reached when the tool-insert end 15 abuts the end of bore 6.

Finally, as shown in FIG. 10c, the blocking body 20 is moved towards the second end 9 of the coupling body 2 until the male drive geometry 30 is completely engaged with the female drive geometry 31. This corresponds to the second position of the locking body 20. The blocking body sphere 34 blocks any inclination of the tool-insert 10 relative to the coupling body 2, hence effectively coupling the tool-insert 10 with the coupling body 2.

Figure 11A:
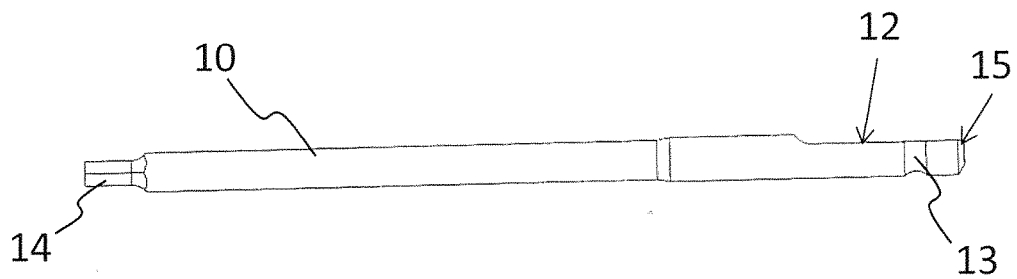
FIGS. 11a-11b an alternative embodiment of a tool-insert.
Figure 11B:
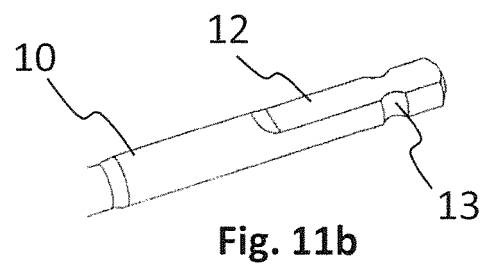

FIGS. 11a and 11b show an alternative embodiment of a tool-insert 10. Rather than comprising a multitude of tool-insert faces 12, the tool-insert 10 according to this embodiment only includes a single tool-insert face 12. This tool-insert face 12 is configured as a flat portion spanning from the tool-insert end 15 towards the tool feature end 14 for a certain length. The tool-insert face 12 according to this embodiment encompasses a part of the groove 13 which therefore does not span around the entire circumference of the tool-insert 10. FIG. 11b shows the tool-insert 12 in more detail in a perspective view, while FIG. 11a represents the tool-insert 10 as viewed from the side.

Figure 12:
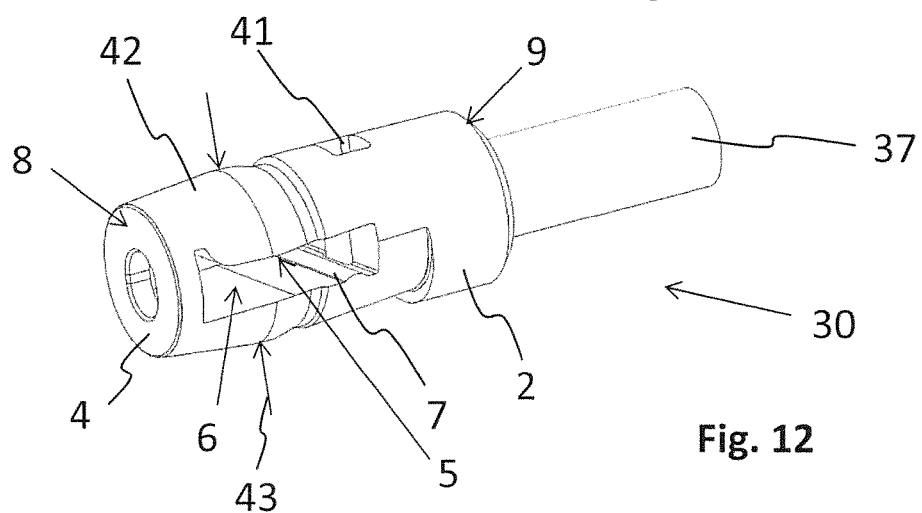
FIG. 12 a second embodiment of a medical power-tool chuck with a coupling device according to the present invention.

FIG. 12 depicts a further embodiment of a medical power-tool chuck 30 according to the present invention. This embodiment of the medical power-tool chuck 30 as shown is intended to be used in connection with a tool-insert 10 according to the embodiment as shown in FIG. 11.

The medical power-tool chuck 30 comprises a coupling body 2 which is generally in the form of a cylinder. However, towards the first end 8, the coupling body 2 includes a conical portion 42. Hence, at its first end 8 the coupling body 2 will have a smaller diameter than its base diameter 43. In the conical portion, the diameter gradually increases from the first end 8 towards the second end 9 until the diameter reaches the base diameter 43. The coupling body 2 is attached to a connection portion 37 at its second end 9. Further, the coupling body 2 includes a bore 6 configured as a blind bore which is open on two opposite sides with the exception of a portion adjacent the first end 8 of the coupling body 2. Further, a pocket 41 is arranged in said coupling body 2, said pocket 41 providing a passage between the outer surface of the coupling body 2 and the bore 6. The bore 6 further includes a protrusion 7 as well as an anti-rotation face 5 arranged on the opposite side of the protrusion 7. Note that in the embodiment shown, the bore 6 is not round—with the exception of the portion adjacent the first end 8 of the coupling body 2—features flat surfaces. One of these surfaces serves as anti-rotation face 5.

Figure 13A:
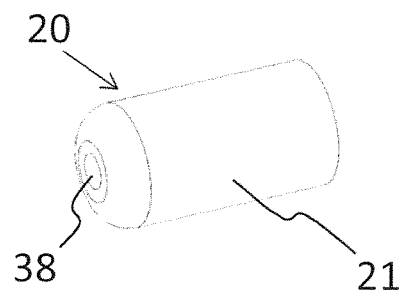
FIGS. 13a-13b a locking body for the medical power-tool chuck according to FIG. 12.
Figure 13B:
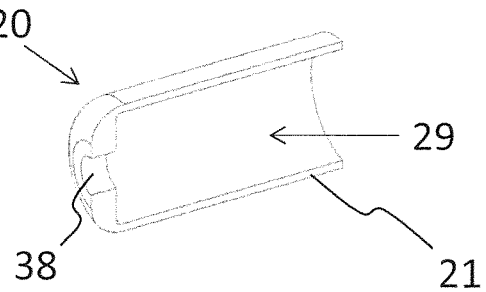

FIGS. 13a and 13b show representations of a locking body 20 to be used in connection with the medical power-tool chuck 30 according to FIG. 12. While FIG. 13a shows a perspective representation of the locking body 20, FIG. 13b shows a sectional view of the locking body 20. The locking body 20 includes a cylindrical hollow body 21 with a lumen 29 and an opening 38 at one end. The opening 38 has a smaller diameter than the diameter of the lumen 29. The diameter of the opening 38 corresponds to the outer diameter of the tool-insert 10 to be used in connection with the medical power tool-chuck 30.

Figure 14A:
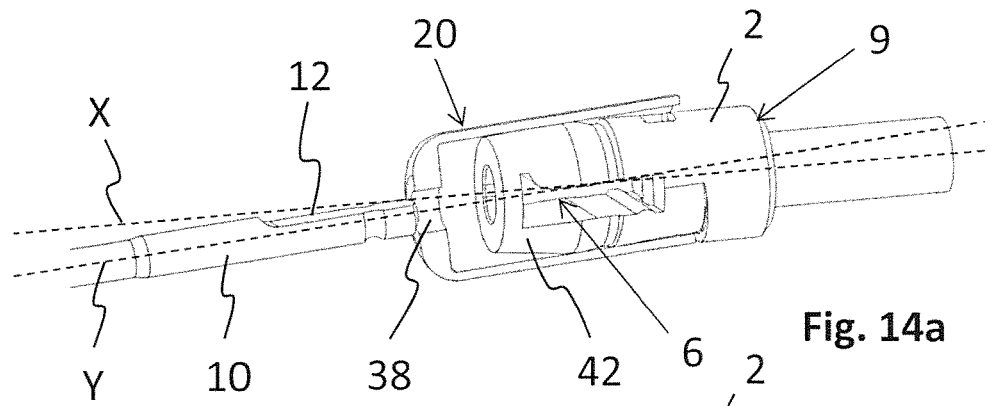
FIGS. 14a-14d the assembly steps of the medical power-tool chuck of FIG. 12 with a tool-insert according to FIG. 11.
Figure 14B:
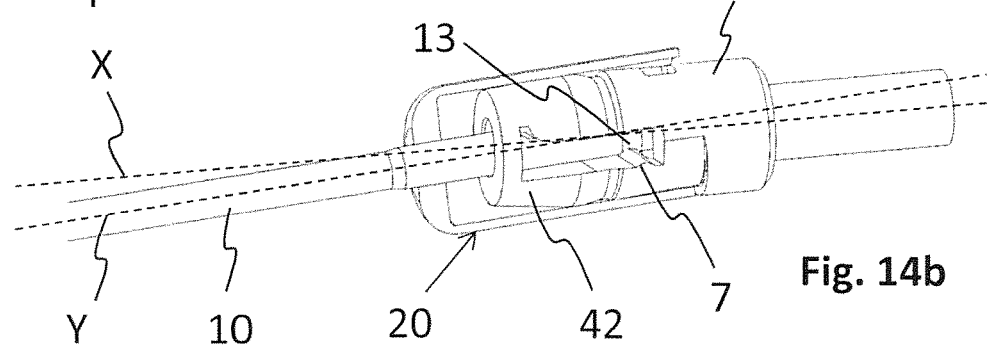
Figure 14C:
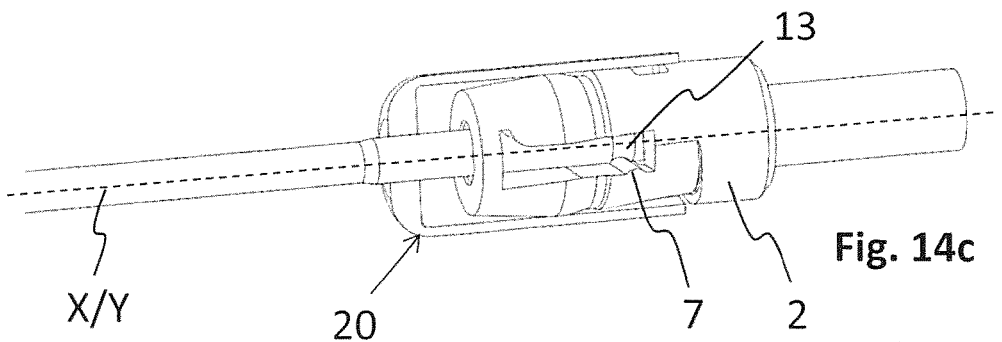
Figure 14D:
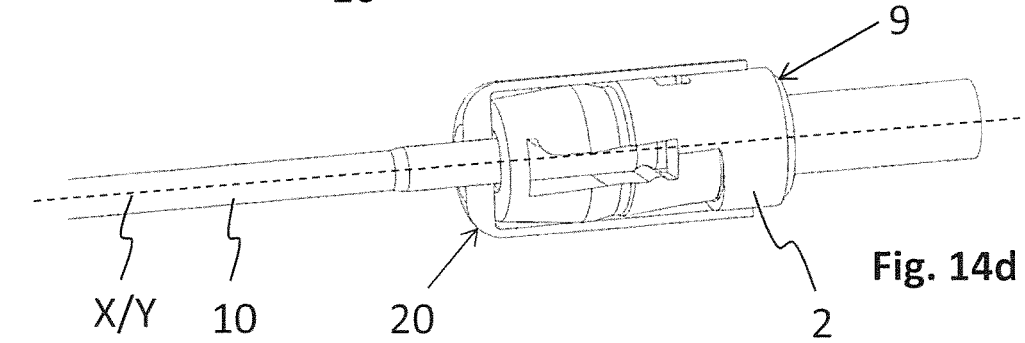

FIGS. 14a-14d show the assembly steps for medical power-tool chuck 30 according to the embodiment of FIG. 12 with a tool-insert 10 according to the embodiment as shown on FIG. 11. The locking body 20 is inserted over the first end 8 of the coupling body 2. Thanks to the conical portion 42, the locking body 20 may be inclined relative to the coupling body 2. The state of the locking body 20 as shown in FIG. 14a corresponds to the first position of the locking body 20. The inclinations allows the insertion of the tool-insert 10 at an angle to the coupling body 2, i.e. the central axis Y of the tool-insert 10 is at an angle with the working axis X of the coupling body 2. The tool insert 10 is first introduced into the opening 38 of the locking body 20 and subsequently into bore 6. The open sides of bore 6 also allow an oblique introduction of tool-insert 10 into bore 6. The tool-insert 10 is subsequently further advanced towards the second end 9 of the coupling body 2, as shown on FIG. 14b. The tool-insert 10 is sized such that upon abutment of the tool-insert 10 on the end of bore 6, the groove 13 is aligned with the protrusion 7. In a next step, as shown on FIG. 14c, the central axis Y of tool insert 10 is re-aligned with the working axis X of the coupling body 2. This results in an engagement of groove 13 with protrusion 7. Further, the locking body 20 is aligned in parallel with the coupling body 2. Finally, the locking body 20 is moved towards the second end 9, as shown on FIG. 14d.

Figure 15A:
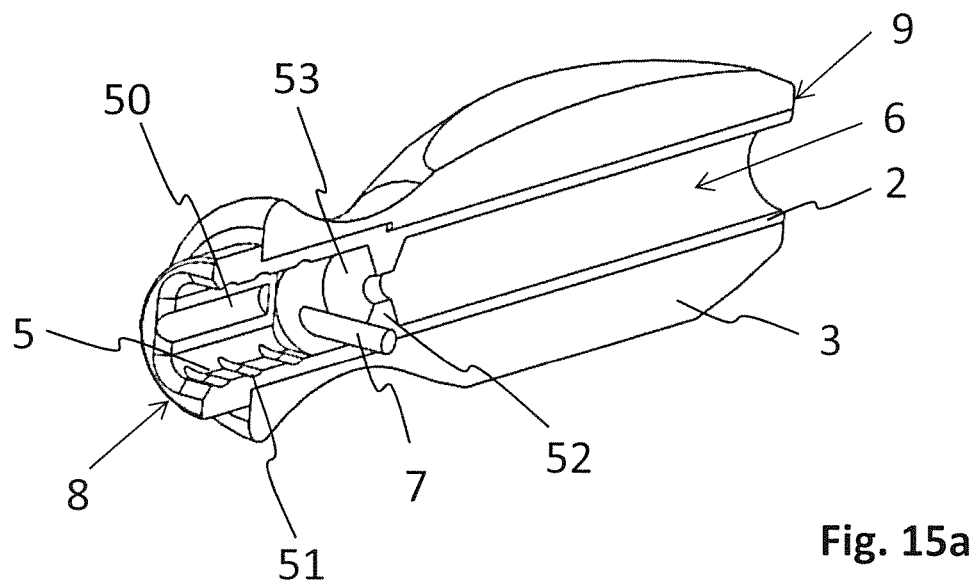
FIGS. 15a-15b a further embodiment of a medical tool according to the present invention.
Figure 15B:
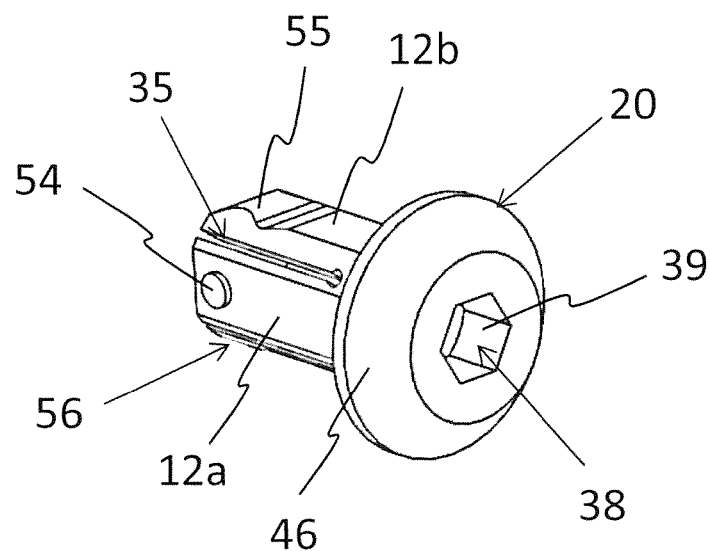

FIGS. 15a and 15b show a further embodiment of a medical tool 1 according to the present invention. FIG. 15a depicts the handle 3 with the coupling body 2 in a sectional cut. Towards the first end 8, the bore 6 comprises additional features when compared to the embodiment according to FIG. 2. Specifically, a constriction feature 52 is arranged past the protrusion 7 in the direction of the second end 9, said constriction feature 52 locally restricting the diameter of the bore 6. Towards the first end 8, said constriction feature 52 includes a conical surface 53. Further, between the first end 8 and the protrusion 7, the bore 6 has a rectangular cross-section, wherein the inner surfaces of said rectangular section of the bore 6 form anti-rotation faces 5. A guiding groove 50 is located on one of the anti-rotation surfaces 5 which is arranged perpendicular to the protrusion 7. The anti-rotation faces 5 which are parallel to said protrusion 7 comprise several notches 51.

FIG. 15b shows a locking-body 20 to be used in connection with the handle 2 according to FIG. 15a. Said locking-body 20 comprises a head section 46 with an opening 38 comprising second anti-rotational faces 39. Further, the locking-body 20 includes a cuboid section 56 with four tool-insert faces 12a, 12b. Said cuboid section includes one nose 54 protruding outwards from a first too-insert face 12a. Further, two cut-outs 35 are provided which impart some flexibility to two second tool-insert faces 15b of the cuboid section 56 which are perpendicular to the first tool-insert face 12a. Said two second tool-insert faces 12b each comprise one bulge 55.

FIGS. 16a to 16d depict the assembly steps of a surgical tool 1 with a handle 3 and coupling body 2 according to FIGS. 15a and 15b with a tool-insert 10 according to FIG. 15b. In a first step, the cuboid section 56 is inserted into the rectangular section of bore 6 from the first end 8, whereby the nose 54 is inserted into the guiding groove 50. Cooperation of the nose 54 with the guiding groove 50 restricts any tilting motion of the blocking body 20 relative to the coupling body 2 around a single axis. The blocking body 20 is tilted such that its central axis Y is at an angle to the working axis X of the coupling body 2. Then the tool insert 10 is inserted into the opening 38 of the blocking body 20.

Figure 16A:
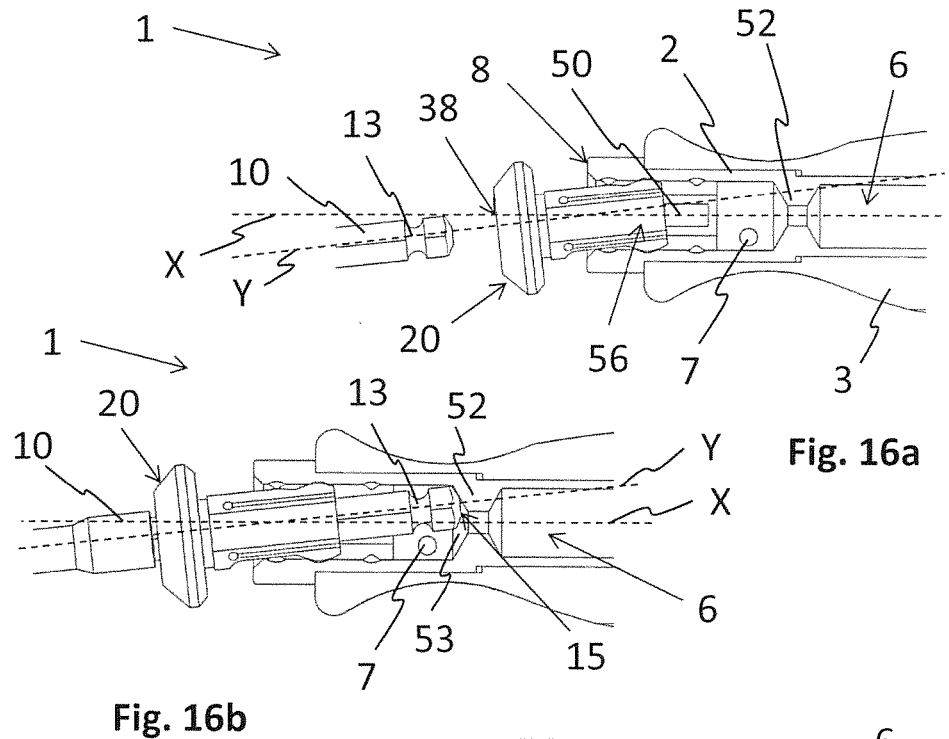
FIGS. 16a-16d assembly steps of a surgical tool according to FIGS. 15a and 15b.
Figure 16B:
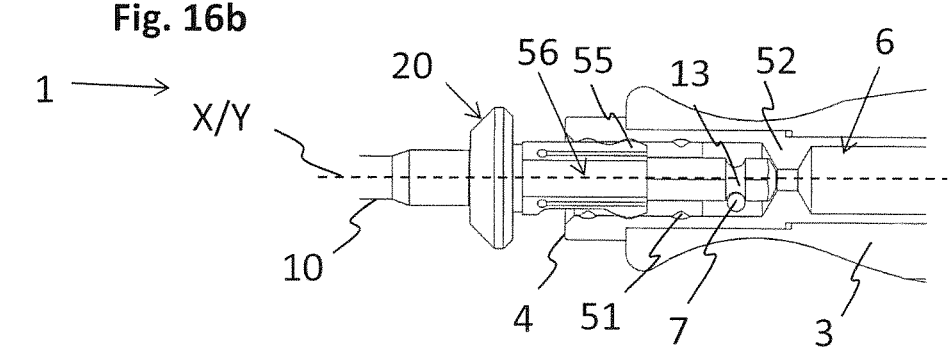
Figure 16C:
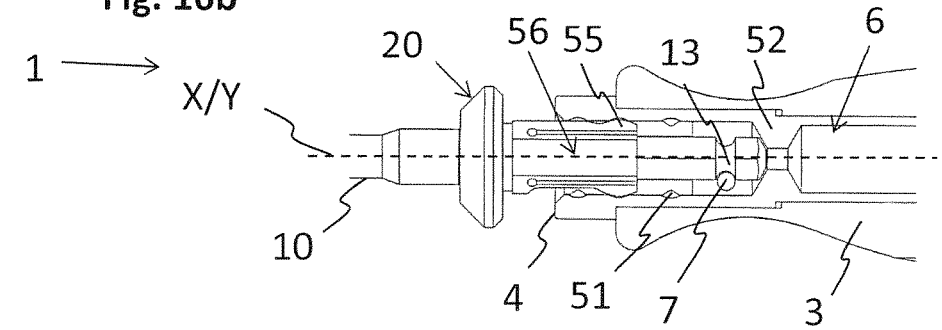
Figure 16D:
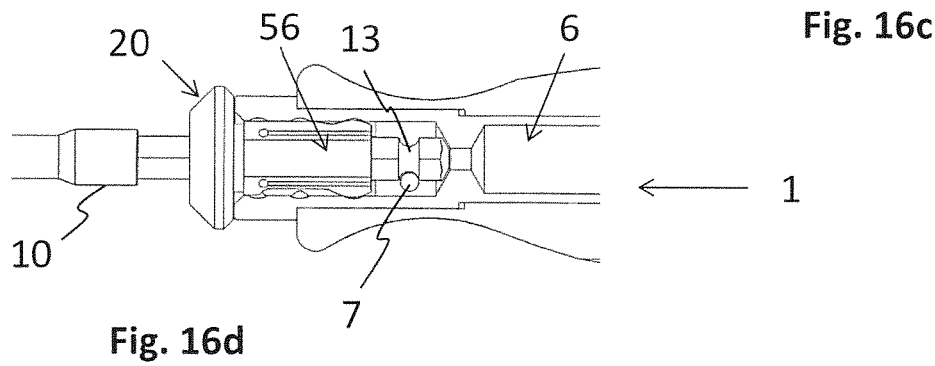

In a second step, as shown in FIG. 16b, the tool-insert 10 is advanced into bore 6 until the tool-insert end 15 abuts the conical surface 53 of the constriction structure 52. Said conical surface 53 helps in guiding the tool-insert end 15 in a swivel motion to a configuration where the central axis Y of the tool-insert 10 is aligned with the working axis X of the coupling body 2. Said alignment engages the groove 13 with the protrusion 7, as shown in FIG. 16c. Concurrently, the cuboid section 56 is likewise aligned with the rectangular section of bore 6 and may be advanced therein, as shown in FIG. 16d. Thereby, the bulges 55 on the cuboid section 56 of the locking body 20 will cooperate with the notches 51 in the rectangular section of the bore 6, thus locking the locking body 20 against any linear movement within the bore 6. Provision of the cut-outs 35 provides sufficient resiliency to the second tool-insert faces 12b such that the bulges 55 may be passed above the notches 51 upon application of a sufficient force onto the locking body 20.

The cooperation of the nose 54 with the guiding groove 50 helps a user of the medical tool 1 to find the correct tilting direction to effect an engagement or a disengagement of the groove 13 and the protrusion 7.

The invention claimed is:

1. A coupling device for a handle of a medical tool or medical power-tool chuck, comprising a coupling-body including a bore, a working axis extending along said bore and a seat arranged at a first end of said bore for receiving a tool-insert with a central axis at a non-zero angle in reference to the working axis, wherein the coupling-body further comprises a protrusion arranged within said bore, the protrusion being configured to allow the tool-insert to advance past the protrusion only when the central axis of the tool-insert is inclined relative to the working axis, and said protrusion being configured to engage a groove of the tool-insert upon alignment of the central axis with the working axis, wherein the engagement of the protrusion with said groove locks the tool-insert within said coupling body.

2. The coupling device of claim 1, further comprising a locking-body being mounted into the bore and axially translatable about the working axis from a first position in a second position, the locking-body locking the central axis of the tool-insert to the working axis in the second position.

3. The coupling device of claim 2, wherein the locking-body comprises a cylindrical hollow body having an outer diameter substantially equivalent to the diameter of the bore and a top portion with an increased diameter, said locking-body being inserted into the bore at a second end arranged opposite to said first end.

4. The coupling device of claim 2, wherein the locking-body is mounted into the bore of the coupling-body at said first end and is configured to be tilted in relation to the working axis in the first position.

5. The coupling device according to claim 4, wherein the coupling body comprises a female drive geometry at its first end and the locking-body includes a male drive geometry adapted to be engaged with said female drive geometry in the second position.

6. The coupling device according to claim 4, wherein the locking body includes an opening for passage of the tool-insert, said opening comprising at least one second anti-rotational face.

7. The coupling body according to claim 5, wherein the locking body further comprises a cylindrical portion linking said male drive geometry with a locking body sphere having a rounded outer surface, said cylindrical portion and said locking body sphere being sized to be inserted into said bore.

8. The coupling device of claim 1, wherein the seat comprises at least one anti-rotation face mating with at least one corresponding tool-insert face on the tool-insert such as to transfer torsional moments between the coupling body and the tool-insert.

9. The coupling device of claim 8, wherein the at least one anti-rotation face is a rounded anti-rotation face comprising a curved surface in the direction of the central axis.

10. The coupling body according to claim 1, wherein the locking body is configured to be slipped over said coupling body at said first end and said coupling body includes a conical portion at its first end.

11. The coupling device of claim 1, wherein said handle and said coupling device are configured as a monobloc structure.

12. The coupling device of claim 1, wherein the protrusion is unitary with the coupling-body.

* * * * *